United States Patent
Yanagisawa et al.

(10) Patent No.: US 9,552,956 B2
(45) Date of Patent: Jan. 24, 2017

(54) RADIATION GENERATING APPARATUS AND RADIATION IMAGING APPARATUS

(75) Inventors: Yoshihiro Yanagisawa, Fujisawa (JP); Shuji Aoki, Yokohama (JP); Miki Tamura, Kawasaki (JP); Kazuyuki Ueda, Tokyo (JP); Ichiro Nomura, Atsugi (JP)

(73) Assignee: CANON KABUSHIKI KAISHA, Tokyo (JP)

(*) Notice: Subject to any disclaimer, the term of this patent is extended or adjusted under 35 U.S.C. 154(b) by 150 days.

(21) Appl. No.: 14/131,859

(22) PCT Filed: Jul. 24, 2012

(86) PCT No.: PCT/JP2012/069519
§ 371 (c)(1),
(2), (4) Date: Jan. 9, 2014

(87) PCT Pub. No.: WO2013/021874
PCT Pub. Date: Feb. 14, 2013

(65) Prior Publication Data
US 2014/0153695 A1   Jun. 5, 2014

(30) Foreign Application Priority Data

Aug. 5, 2011 (JP) .................................. 2011-171610
Nov. 7, 2011 (JP) .................................. 2011-243055

(51) Int. Cl.
*H01J 35/12* (2006.01)
*H05G 1/02* (2006.01)
(Continued)

(52) U.S. Cl.
CPC .............. *H01J 35/12* (2013.01); *G01N 23/04* (2013.01); *H01J 35/16* (2013.01); *H05G 1/025* (2013.01);
(Continued)

(58) Field of Classification Search
CPC ............ H01J 35/00; H01J 35/02; H01J 35/04; H01J 35/08; H01J 35/12; H01J 35/16; H01J 2235/122; H01J 2235/166; H01J 2235/186; G01N 23/04; H05G 1/025; H05G 1/04
(Continued)

(56) References Cited

U.S. PATENT DOCUMENTS 4,250,425 A    2/1981  Gabbay et al. ................ 378/125
4,292,563 A    9/1981  Gabbay et al. ................. 313/56
(Continued)

FOREIGN PATENT DOCUMENTS

CN    2134771       5/1993
CN    1391870       1/2003
(Continued)

OTHER PUBLICATIONS

Engineering Toolbox Thermal Conductivity Table (http://www.engineeringtoolbox.com/thermal-conductivity-d_429.html).*
(Continued)

*Primary Examiner* — David E Smith
(74) *Attorney, Agent, or Firm* — Fitzpatrick, Cella, Harper & Scinto

(57) ABSTRACT

A radiation generating apparatus includes: an envelope 1 having a first window 2 through which a radiation is transmitted; and a radiation tube 10 being held within the envelope 1, and having a second window 15 which is arranged in opposition to the first window 2, and through which the radiation is transmitted; and a radiation shielding member 16 thermally connected to the second window 15, having a radiation transmitting hole 21 arranged in communication with the second window 15, and having a protruding portion protruding from the second window 15 toward the first window 2. A thermally conductive member 17

(Continued)

having a higher thermal conductivity rather than that of the radiation shielding member 16 is connected to the protruding portion of the radiation shielding member 16. The radiation generating apparatus can shield an unnecessary radiation and cool a target with a simple structure and is entirely reduced in weight.

17 Claims, 4 Drawing Sheets

(51) Int. Cl.
    *H05G 1/04*     (2006.01)
    *G01N 23/04*     (2006.01)
    *H01J 35/16*     (2006.01)

(52) U.S. Cl.
    CPC ........... *H05G 1/04* (2013.01); *H01J 2235/122* (2013.01); *H01J 2235/166* (2013.01); *H01J 2235/186* (2013.01)

(58) Field of Classification Search
    USPC .................. 378/121, 127, 128, 130, 140–142
    See application file for complete search history.

(56) References Cited

U.S. PATENT DOCUMENTS

| | | | | |
|---|---|---|---|---|
| 5,878,110 | A * | 3/1999 | Yamamoto | H01J 35/08 378/121 |
| 5,949,849 | A * | 9/1999 | Hirano | H01J 35/18 378/121 |
| 6,041,100 | A * | 3/2000 | Miller | H01J 35/101 378/141 |
| 6,594,341 | B1 * | 7/2003 | Lu | H01J 35/18 378/140 |
| 8,472,585 | B2 | 6/2013 | Ogura et al. | 378/111 |
| 2002/0191734 | A1 | 12/2002 | Kojima et al. | 439/125 |
| 2003/0021377 | A1 | 1/2003 | Turner et al. | 378/102 |
| 2005/0053188 | A1 | 3/2005 | Gohno | 378/15 |
| 2006/0008057 | A1 | 1/2006 | Daniel | 378/203 |
| 2006/0193440 | A1 * | 8/2006 | Radley | G01N 23/12 378/141 |
| 2008/0043919 | A1 | 2/2008 | Chapin et al. | 378/119 |
| 2009/0010393 | A1 | 1/2009 | Klinkowstein et al. | 378/140 |
| 2009/0232270 | A1 | 9/2009 | Okunuki et al. | 378/5 |
| 2010/0046715 | A1 * | 2/2010 | Freudenberger | G21F 1/00 378/140 |
| 2012/0140895 | A1 | 6/2012 | Okunuki et al. | 378/122 |
| 2012/0307974 | A1 | 12/2012 | Yamazaki et al. | 378/62 |
| 2012/0307978 | A1 | 12/2012 | Yamazaki et al. | 378/121 |
| 2013/0016810 | A1 | 1/2013 | Tamura et al. | 378/62 |
| 2013/0016811 | A1 | 1/2013 | Ueda et al. | 378/62 |
| 2013/0016812 | A1 | 1/2013 | Yanagisawa et al. | 367/62 |
| 2013/0034207 | A1 | 2/2013 | Aoki et al. | 378/62 |
| 2013/0148781 | A1 | 6/2013 | Yamazaki et al. | 378/62 |
| 2013/0230143 | A1 | 9/2013 | Ueda et al. | 378/62 |
| 2013/0235975 | A1 | 9/2013 | Tamura et al. | 378/62 |
| 2014/0140480 | A1 | 5/2014 | Ogura et al. | 378/140 |
| 2014/0140486 | A1 * | 5/2014 | Yanagisawa | H01J 35/12 378/141 |

FOREIGN PATENT DOCUMENTS

| | | | |
|---|---|---|---|
| CN | 1593344 | 3/2005 | |
| CN | 1794899 | 6/2006 | |
| CN | 101128081 | 2/2008 | |
| CN | 101521136 | 9/2009 | |
| FR | 2 415 876 A1 | 8/1979 | |
| FR | 2415876 A1 * | 8/1979 | ............. H01J 35/18 |
| FR | 2415876 A * | 9/1979 | |
| GB | 762375 A * | 11/1956 | ............. H01J 35/16 |
| JP | 2004-235113 A | 8/2004 | |
| JP | 2005-523558 | 8/2005 | |
| JP | 2007-265981 A | 10/2007 | |
| JP | 2009-043651 | 2/2009 | |
| JP | 2013-055041 | 3/2013 | |
| JP | 2013-122906 | 6/2013 | |

OTHER PUBLICATIONS

Office Action issued May 28, 2015 in Chinese Application 2001280037297.8, with translation.

Office Action issued Jun. 15, 2015 in Chinese Application 2001280037295.9, with translation.

Office Action issued on Jan. 30, 2015 by Korean IPO in counterpart Korean patent application 10-2014-7498; English summary of technical comments by Korean Examiner attached.

\* cited by examiner

RADIATION GENERATING APPARATUS AND RADIATION IMAGING APPARATUS

TECHNICAL FIELD

The present invention relates to a radiation generating apparatus used for non-destructive X-ray imaging in the fields of medical devices and industrial devices, and a radiation imaging apparatus using the radiation generating apparatus.

BACKGROUND ART

Generally, a radiation tube accelerates an electron emitted from an electron emitting source at high voltage to irradiate a target with the electron to generate radiation such as an X-ray. The radiation generated at this time is emitted in all directions. PTL 1 discloses a transmission X-ray generation apparatus in which X-ray shielding members are placed on an electron incident side and an X-ray emission side of a target to shield unnecessary X-rays.

In order to generate a radiation suitable for radiation imaging, a high voltage needs to be applied between an electron emitting source and a target to irradiate the target with an electron beam with high energy. However, generally, generation efficiency of radiation is extremely low, and about 99% of consumed power generates heat at the target. Since the generated heat increases the temperature of the target, a unit for preventing heat damage to the target is required. PTL 2 discloses an X-ray generation tube in which a cooling mechanism is provided around an X-ray transmission window to increase heat radiation efficiency of the target.

CITATION LIST

Patent Literature

PTL 1: Japanese Patent Application Laid-Open No. 2007-265981
PTL 2: Japanese Patent Application Laid-Open No. 2004-235113

SUMMARY OF INVENTION

Technical Problem

In imaging with a short time pulse and a large tube current in the medical field or imaging with a small focal point of an electron beam in the industrial field, the temperature of the target may instantaneously increase. In such a case, heat radiation via only a conventional radiation shielding member is insufficient.

If the radiation shielding member is increased in thickness to increase heat radiation properties, the radiation generating apparatus as a whole is increased in weight because the radiation shielding member is generally made of heavy metal. Also, providing a cooling mechanism separately from the radiation shielding member makes it difficult to reduce the size of the radiation generating apparatus as a whole.

Thus, the present invention has an object to provide a radiation generating apparatus that can shield an unnecessary radiation and cool a target with a simple structure and that yet is reduced in weight, and a radiation imaging apparatus using the radiation generating apparatus.

Solution to Problem

In order to solve the above problem, according to an aspect of the present invention, a radiation generating apparatus comprises: an envelope having a first window through which radiation is transmitted; and a radiation tube held within the envelope, and having a second window which is arranged in opposition to the first window, and through which the radiation is transmitted, wherein the radiation tube has a radiation shielding member having a protruding portion protruding from the second window toward the first window, and a thermally conductive member having a higher thermal conductivity than that of the radiation shielding member is connected to the protruding portion of the radiation shielding member.

Advantageous Effects of Invention

According to the present invention, shielding performance of an unnecessary radiation can be ensured, and heat of the target can be effectively radiated. Further, a thermally conductive member having a lower density than a radiation shielding member is used, thereby allowing an entire radiation generating apparatus to be reduced in weight. This allows radiation imaging with a large tube current and a small focal point, thereby obtaining a captured image with high resolution. Also, with a reduced weight, the apparatus can be easily applied to home medical tests and on-site medical tests for emergency use.

Further features of the present invention will become apparent from the following description of exemplary embodiments with reference to the attached drawings.

DESCRIPTION OF EMBODIMENTS

Now, embodiments of the present invention will be described with reference to the drawings.

Figure 1:
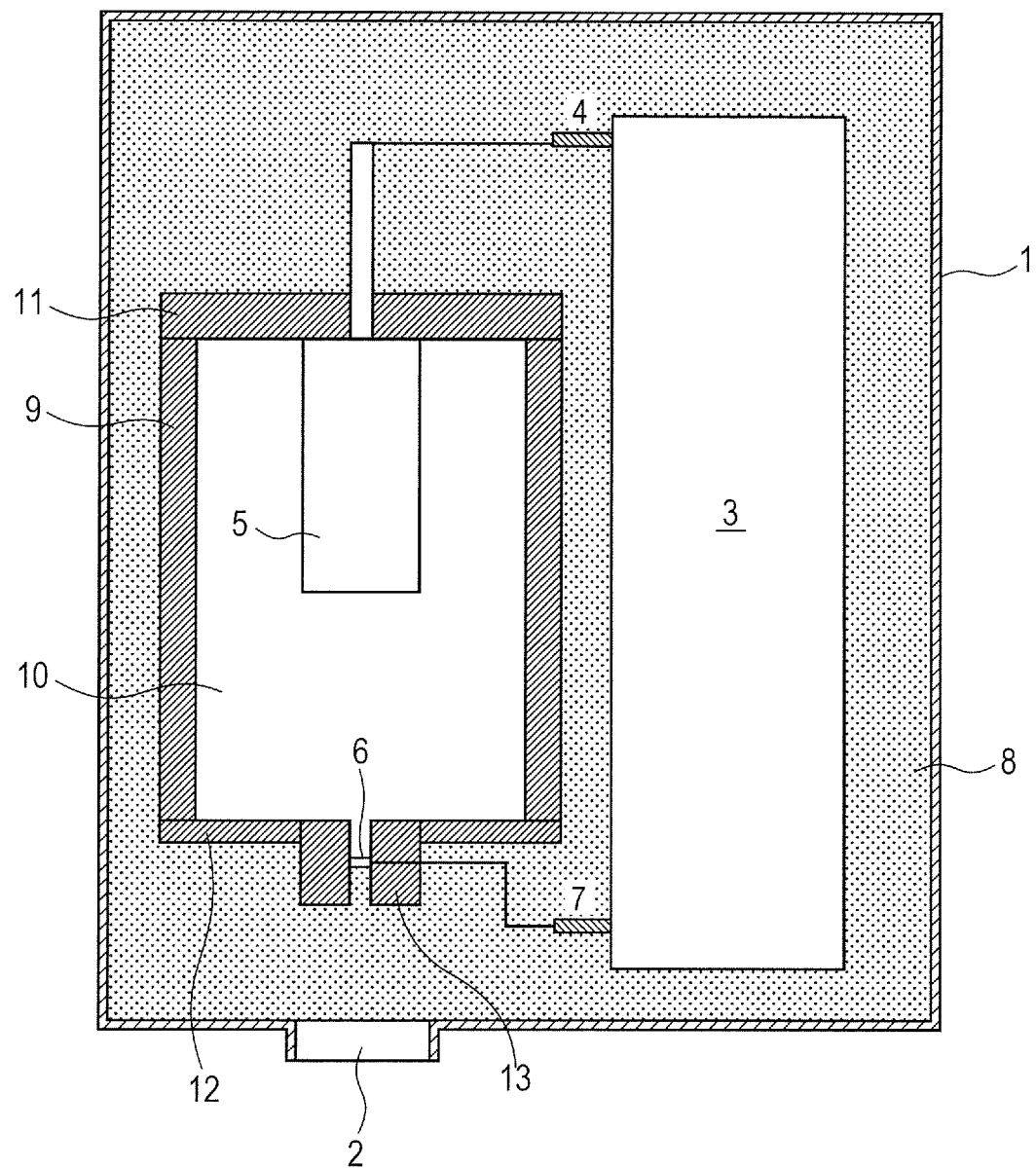
FIG. 1 is a schematic sectional view showing a radiation generating apparatus of the present invention.

FIG. 1 is a schematic sectional view showing an embodiment of a radiation generating apparatus of the present invention. The envelope 1 holds therein a transmission radiation tube 10 and a voltage control portion 3 (voltage control unit). An extra space (between an inner wall of the envelope 1 and the radiation tube 10) in the envelope 1 is filled with an insulating fluid 8.

A voltage control portion 3 includes a circuit board and an insulation transformer, and outputs a signal to control generation of a radiation via a terminal 4 to an electron emitting source 5 in the radiation tube 10. The potential of an anode portion 12 is determined via a terminal 7.

The envelope 1 may have sufficient strength as a container, and is made of metal or a plastic material.

The insulating fluid 8 is a liquid or a gas having electrically insulating properties placed as a cooling medium. The liquid preferably includes electrically insulating oil. The electrically insulating oil favorably includes mineral oil, silicone oil, or the like. A different usable insulating fluid 8 includes a fluorinated electrically insulating liquid. The gas includes atmospheric gas, and using gas can reduce weight of the apparatus as compared to when using an insulating liquid.

The envelope 1 includes a first window 2 through which radiation is transmitted and taken out of the envelope. Radiation emitted from the radiation tube 10 is emitted to the exterior through the first window 2. The first window 2 is made of glass, aluminum, beryllium, or the like.

The radiation tube 10 includes a cylindrical evacuated container 9 as an outer frame, an electron emitting source 5 placed therein, a target portion 6, and a window member 8.

The evacuated container 9 maintains the inside of the radiation tube 10 in a vacuum state, and a body portion thereof is made of an insulating material such as glass or ceramic. A cathode portion 11 and an anode portion 12 are made of a conductive alloy (Kovar). The degree of vacuum inside the evacuated container 9 may be about $10^{-4}$ to $10^{-8}$ Pa. A getter (not illustrated) may be placed in the evacuated container 9 to maintain the vacuum. The evacuated container 9 includes a cylindrical opening in the anode portion 12, and a cylindrical window member 13 is joined to the opening. The window member 13 has a cylindrical radiation transmitting hole (hereinafter simply referred to as a transmitting hole) 21 through which a part of the radiation (X-rays in this embodiment) generated in the target portion 6 is transmitted. The cylindrical target portion 6 is joined to an inner wall of the transmitting hole 21 to seal the evacuated container 9.

The electron emitting source 5 is placed to face the target portion 6 in the evacuated container 9. The electron emitting source 5 may be formed of a tungsten filament, a hot cathode such as an impregnated cathode, or a cold cathode such as a carbon nanotube. An extraction electrode is placed in the electron emitting source 5, an electron emitted by an electric field formed by the extraction electrode is converged by a lens electrode to enter the target 6 and generate a radiation. At this time, an accelerating voltage of about 40 to 120 kV is applied between the cathode portion 11 electrically connected to the electron emitting source 5 and the anode portion 12 electrically connected to a target 14 depending on intended use of a radiation.

FIG. 2 is a schematic sectional view showing, in an enlarged manner, a surrounding part of the window member 13 in FIG. 1.

The target portion 6 includes the target 14 and a substrate 15 as a second window. The target 14 is placed on a surface of the second window 15 at the electron emitting source side. The target 14 is preferably made of a material having a high melting point and high radiation generation efficiency. For example, tungsten, tantalum, molybdenum, or the like can be used. In order to reduce absorption of generated radiation as the radiation is transmitted through the target 14, an appropriate thickness of the target 14 is about several μm to several tens of μm.

The second window 15 supports the target 14, and transmits at least a part of the radiation generated in the target 14, and is placed in a position facing the first window 2 in the radiation transmitting hole 21 in the window member 13. The second window 15 is preferably made of a material having strength to support the target 14 and scarcely absorb the radiation generated in the target 14, and having high thermal conductivity so as to quickly radiate heat generated in the target 14. For example, diamond, silicon nitride, or aluminum nitride may be used. To satisfy the above requirement for the second window 15, an appropriate thickness of the second window 15 is about 0.1 mm to several mm.

Figure 2A:
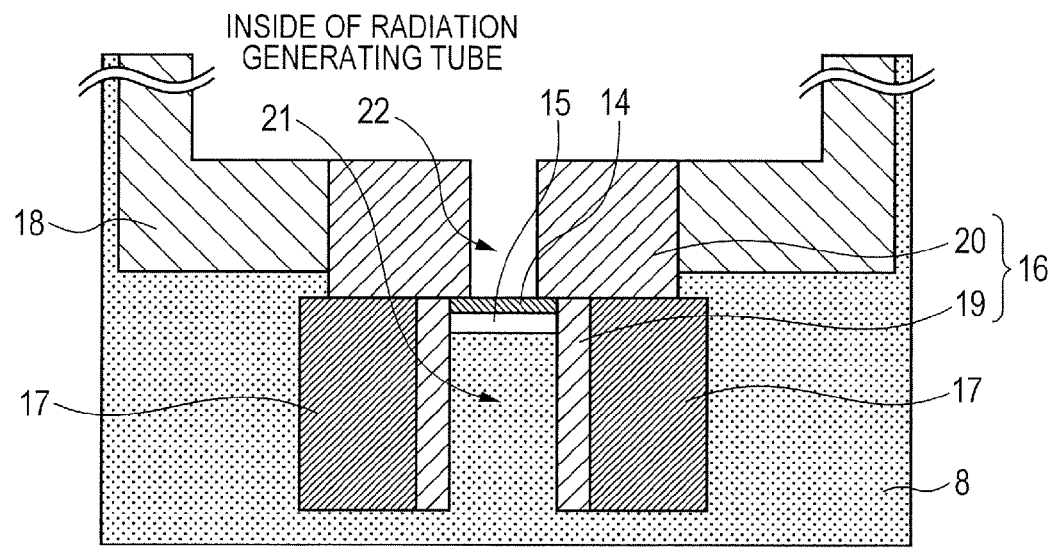
FIGS. 2A, 2B and 2C are schematic sectional views of a surrounding part of a radiation shielding member according to an embodiment of the present invention.

As illustrated in FIG. 2A, the window member 13 includes a radiation shielding member (hereinafter simply referred to as a shielding member) 16, and a thermally conductive member 17. The shielding member 16 has the transmitting hole 21 arranged in communication with the second window 15, and shields that portion of the radiation emitted from the target 14 that is not necessary for use. The shielding member 16 includes two shielding members (a first shielding member 19 and a second shielding member 20). The first shielding member 19 and the second shielding member 20 may be made of the same material, and may be integrally formed and placed or separately placed. The first shielding member 19 and the second shielding member 20 may be made of different materials, and may be integrally placed by joining or separately placed. The second window 15 is secured to the shielding member 16 to maintain vacuum airtightness of the evacuated container 9, and silver soldering is used as such a securing unit.

The first shielding member 20 is placed to protrude from the second window 15 toward the electron emitting source 5, and has an electron transmitting hole 22 arranged in communication with the second window 15. An electron emitted from the electron emitting source 5 passes through the electron transmitting hole 22 and collides with the target 14. Of the radiation generated in the target 14, the radiation scattered on the electron emitting source side of the target 14 is shielded by the first radiation shielding member 20.

The second shielding member 19 is placed to protrude from the second window 15 toward the first window 2, and has the transmitting hole 21 arranged in communication with the second window 15. Radiation that has been transmitted through the second window 15 passes through the transmitting hole 21, and an unnecessary radiation is shielded by the second shielding member 19.

In terms of taking out a larger dose of radiation to an outside of the envelope 1, an opening area of the transmitting hole 21 preferably gradually increases from the second window 15 toward the first window 2. This is because the radiation that has been transmitted through the second window 15 is radiating out.

The center of the electron transmitting hole 22 in the first shielding member 20, the center of the transmitting hole 21 in the second shielding member 19, and the center of the target 14 are preferably on the same line. This is because such arrangement allows radiation generated by irradiation of the transmission target 14 with an electron to be reliably taken out in a larger dose.

The shielding member 16 is preferably made of a material having high radiation absorption and high thermal conductivity. For example, a metal material such as tungsten, tantalum, or an alloy thereof may be used. To sufficiently shield unnecessary radiation, appropriate thicknesses of the first shielding member 20 and the second shielding member 19 are about 0.5 to 5 mm depending on the set accelerating voltage of the electrons.

Figure 2B:
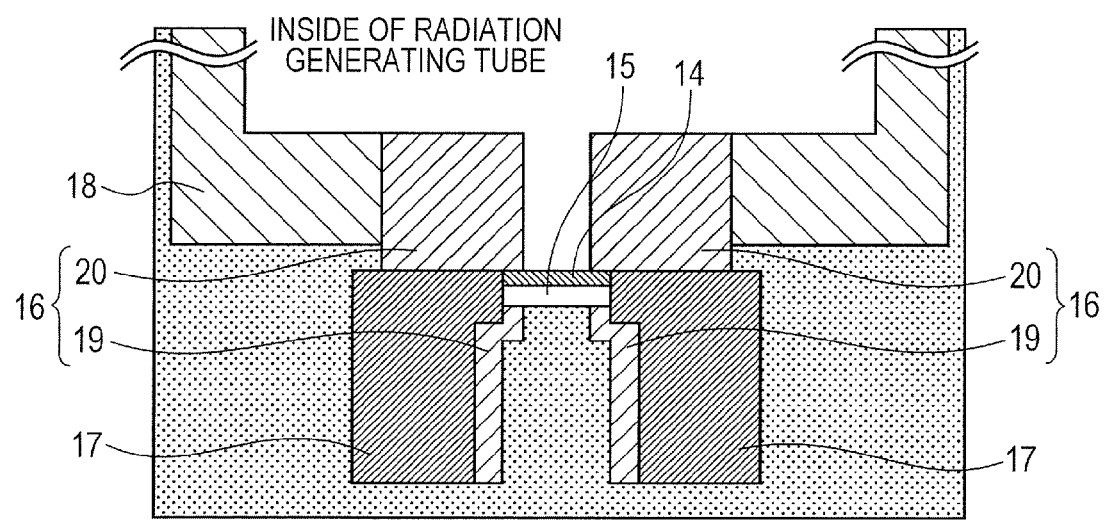

As illustrated in FIGS. 2A and 2B, the thermally conductive member 17 is placed to surround the second shielding member 19 on an outer peripheral side of the second shielding member 19. The thermally conductive member 17 is joined to the second shielding member 19 by brazing, casting, soldering, welding, laser welding, screw-in, burn fitting, taper fitting, or an adhesive, or be mechanically screwed shut. The thermally conductive member 17 and the second shielding member 19 have cylindrical shapes having the same central axis, and the thermally conductive member 17 has a larger radial thickness than the second shielding member 19.

Figure 2C:
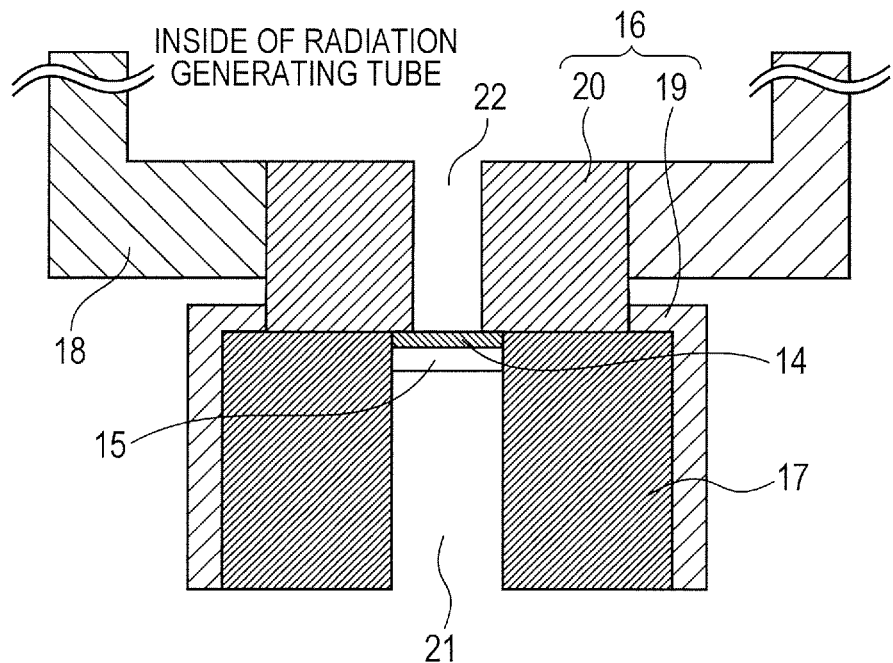

As illustrated in FIG. 2C, the thermally conductive member 17 may be placed on an inner peripheral side of the second shielding member 19 so that the second shielding member 19 surrounds the thermally conductive member 17. Also in this case, the shielding member 16 includes two shielding members (a first shielding member 19 and a second shielding member 20). The first shielding member 19 and the second shielding member 20 may be made of the same material and integrally formed, or made of different materials and formed by joining. The shielding member 16 is in contact with the outer periphery of the thermally conductive member 17.

The thermally conductive member 17 is preferably made of a material having higher thermal conductivity than the shielding member 16 and high heat resistance, and may be selected from metal materials, carbon materials, ceramic or the like. The metal materials may include silver, copper, aluminum, cobalt, nickel, iron, or the like, or alloys or oxides thereof. The carbon materials may include diamond, graphite, or the like. The ceramic may include aluminum nitride, silicon carbide, alumina, silicon nitride, or the like. Further, the thermally conductive member 17 is desirably made of a material having a lower density than the radiation shielding member 16.

As the thermally conductive member 17, a material having a lower density than the shielding member 16 is used, thereby reducing weight as compared to the case where the window member 13 includes only the shielding member 16.

Heat generated in the target 14 is directly transferred to the thermally conductive member 17 directly or through the second window 15, or transferred to the thermally conductive member 17 via the shielding member 16. Further, the heat is transferred to an insulating fluid in contact with the thermally conductive member 17 and quickly radiated, thereby preventing a temperature increase of the target 14. Since the thermal conductivity of the thermally conductive member 17 is higher than the thermal conductivity of the shielding member 16, a speed of heat radiation is increased as compared to the case where the window member 13 includes only the shielding member 16.

Figure 3A:
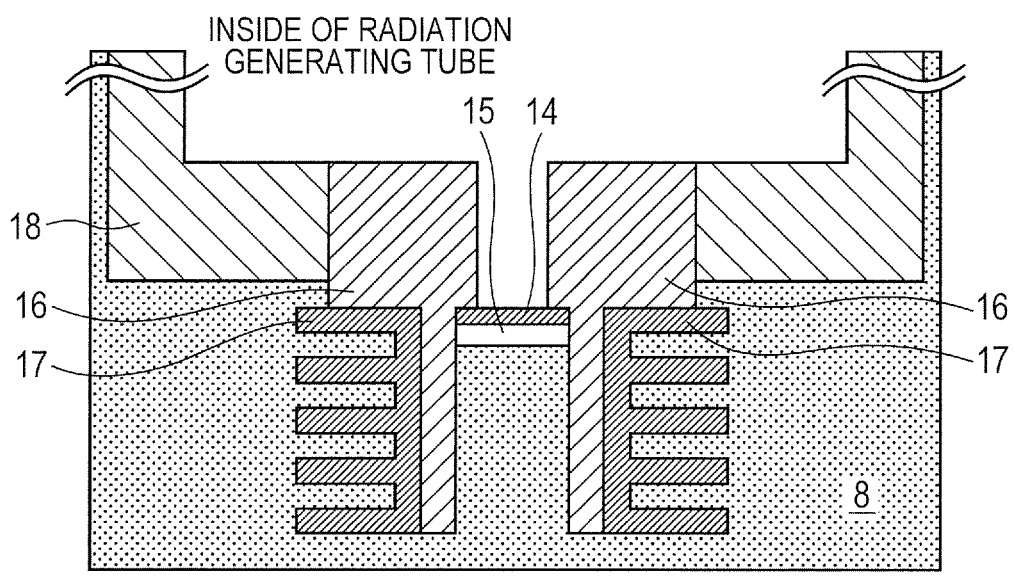
FIGS. 3A and 3B are schematic sectional views of a surrounding part of a radiation shielding member according to another embodiment of the present invention.
Figure 3B:
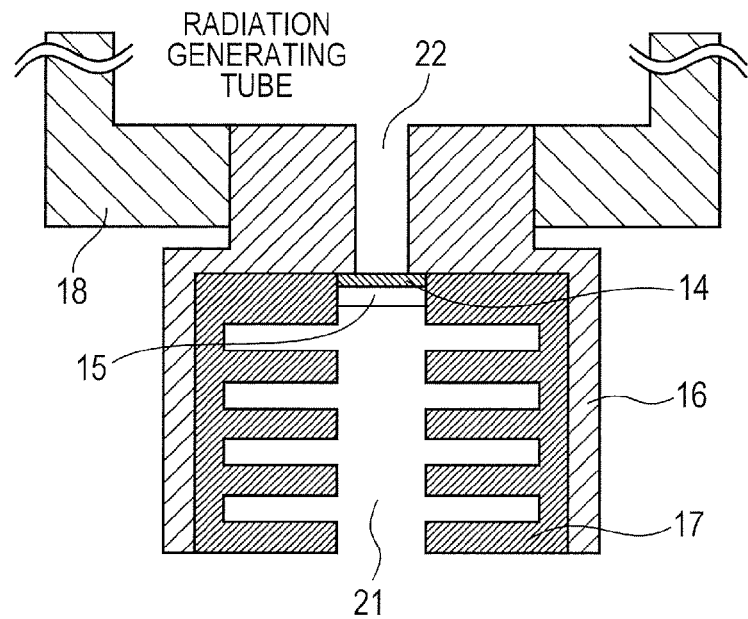

Further, as illustrated in FIGS. 3A and 3B, when the thermally conductive member 17 has a fin structure, an area of the thermally conductive member 17 in contact with the insulating fluid is increased, thereby allowing more effective heat radiation.

The thermally conductive member 17 may be partially placed on an outer periphery or an inner periphery of the second shielding member 19 rather than surrounding the entire outer periphery or inner periphery.

Also, to further increase heat radiation properties, the shielding member 16 and the thermally conductive member 17 are preferably placed so that the target member 6 protrudes toward the first window 2 beyond an end surface position of the evacuated container 9.

As a method for applying an accelerating voltage, either an anode grounding system or a neutral grounding system may be used. The anode grounding system is a system in which when the voltage applied between the target 14 and the electron emitting source 5 is Va [V], the potential of the target 14 as an anode is set to ground (0 [V]), and the potential of the electron emitting source 5 with respect to the ground is set to −Va [V]. Meanwhile, the neutral grounding system is a system in which the potential of the target 14 with respect to the ground is set to +(Va−α) [V], and the potential of the electron emitting source 5 with respect to ground is set to −α [V] (where Va>α>0). The value of α is within a range of Va>α>0, and generally close to Va/2. The neutral grounding system is used to reduce the absolute value of the potential with respect to the ground, thereby reducing creepage distance. (The creepage distance is herein a distance between the voltage control portion 3 and the envelope 1 and a distance between the radiation tube 10 and the envelope 1. If the creepage distance can be reduced, the size of the envelope 1 can be reduced, and thus the weight of the insulating fluid 8 can be reduced, thereby further reducing size and weight of the radiation generating apparatus.)

Example 1

As illustrated in FIG. 2A, tungsten was selected as the shielding member 16 including the first shielding member 19 and the second shielding member 20 integrally formed, and copper was selected as the thermally conductive member 17. The thermally conductive member 17 was secured by brazing to an outer peripheral side of a portion of the shielding member 16 having a protruding portion protruding from the second window 15 toward the first window 2. As the insulating fluid 8, insulation oil including mineral oil was used. As the voltage control system, a neutral grounding system was used. As the electron emitting source 5, a tungsten filament was used and heated by a heating unit (not illustrated) to emit an electron. The emitted electron was accelerated to high energy by electron beam trajectory control by distribution of potentials effected by voltages applied to an extraction electrode and a lens electrode, and the voltage Va applied between the electron emitting source 5 and the target 14 and caused to collide with the target to generate radiation. As the target 14, sheet tungsten was used. To set 50[V] to the extraction electrode, 1000 [V] to the lens electrode, and Va in a neutral grounding system to 100 [kV], the voltage of the target 14 was set to +50 [kV], and the voltage of the electron emitting source 5 was set to −50 [kV].

Example 2

As illustrated in FIG. 2B, in this example, the first shielding member 19 and the second shielding member 20 are separately placed, and the thermally conductive member 17 is placed on the outer peripheral side of the first shielding member 19 so as to be partially in direct contact with the second window 15. This example has a similar configuration to that of Example 1 except for this point. A part of heat generated in the second window 15 is directly transferred to the thermally conductive member 17 without via the first shielding member 19, thereby further increasing the speed of heat radiation.

Example 3

This example is similar to Example 1 except that molybdenum is selected as the shielding member 16, and aluminum is selected as the thermally conductive member 17, and sheet molybdenum is used as the target 14. This example is different from Example 1 in using an anode grounding system as a voltage control system. To set 50[V] to an extraction electrode, 3000 [V] to a lens electrode, and Va in the anode grounding system to 50 [kV], the voltage of the target 14 was set to +50 [kV] and the voltage of the electron emitting source 5 was set to 0 [kV].

Example 4

This example is similar to Example 1 except that tungsten is selected as the shielding member 16, and SiC or graphite sheet is selected as the thermally conductive member 17.

Example 5

This example is similar to Example 1 except that an alloy of tungsten and molybdenum (ratio of components: 90% tungsten and 10% molybdenum) is selected as the shielding member 16, and an alloy of copper and aluminum (ratio of components: 90% copper and 10% aluminum) is selected as the thermally conductive member 17.

Example 6

This example is similar to Example 1 except that tungsten is selected as the shielding member 16, and fin-shaped copper illustrated in FIG. 3A is selected as the thermally conductive member 17.

Example 7

In this example, as illustrated in FIG. 2C, the thermally conductive member 17 was placed on an inner peripheral side of the shielding member 16 having a protruding portion protruding from the second window 15 toward the first window 2. The second window 15 was connected by brazing to an inner wall of the transmitting hole 21 formed in the thermally conductive member 17. Tungsten was selected as the shielding member 16, and copper was selected as the thermally conductive member 17.

Example 8

This example is similar to Example 7 except that copper having a fin structure in FIG. 3B is selected as the thermally conductive member 17.

In each of the above examples, the radiation generating apparatus was able to be satisfactorily handled. Radiation was emitted under the above conditions, and the dose of the generated radiation was measured. Thus, it was confirmed that a stable dose of radiation could be obtained. At this time, unnecessary radiation does not leak, and there was no damage to the target.

Example 9

Figure 4:
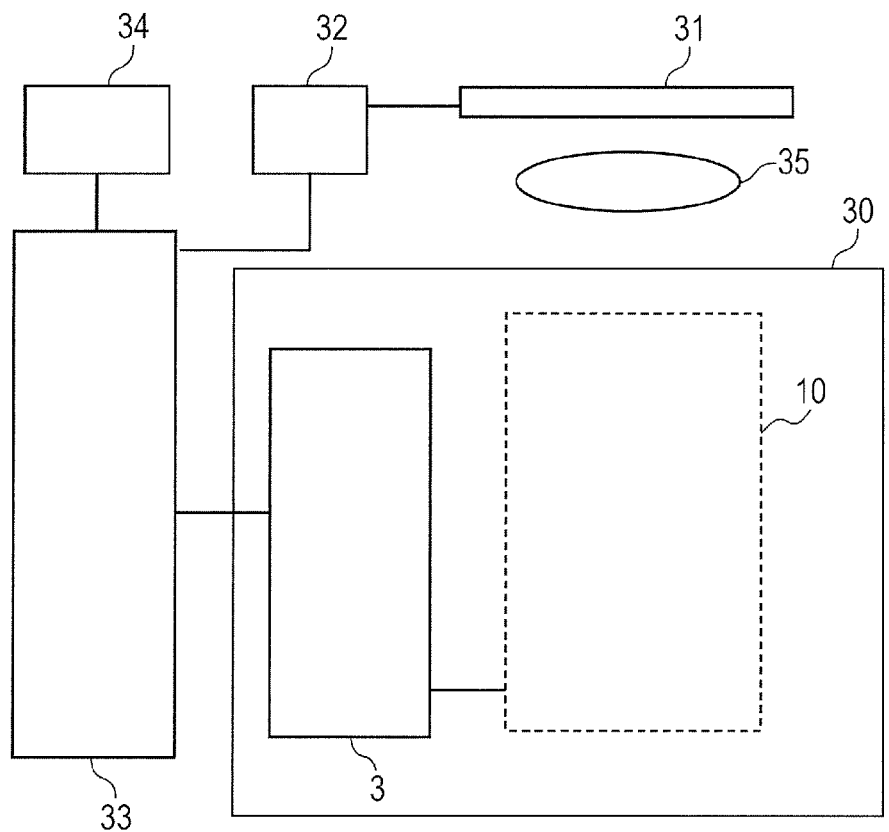
FIG. 4 is a configuration diagram of a radiation imaging apparatus using a radiation generating apparatus of the present invention.

Next, with reference to FIG. 4, a radiation imaging apparatus using the radiation generating apparatus of the present invention will be described. The radiation imaging apparatus of this example includes a radiation generating apparatus 30, a radiation detector 31, a signal processor 32, an apparatus control portion 33, and a display portion 34. As the radiation generating apparatus 30, for example, the radiation generating apparatus in Examples 1 to 9 are favorably used. The radiation detector 31 is connected via the signal processor 32 to the apparatus control portion 33, and the apparatus control portion 33 is connected to the display portion 34 and the voltage control portion 3. Processes in the radiation generating apparatus 30 are collectively controlled by the apparatus control portion 33. The apparatus control portion 33 controls the radiation generating apparatus 30 and the radiation detector 31 in combination. A radiation emitted from the radiation generating apparatus 30 is detected via an object 35 by the radiation detector 31, and a radiation transmission image of the object 35 is captured. The captured radiation transmission image is displayed on the display portion 34. The apparatus control portion 33 controls driving of the radiation generating apparatus 30, and controls a voltage signal applied via the voltage control portion 3 to the radiation tube 10.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2011-171610, filed Aug. 5, 2011 and No. 2011-243055, filed Nov. 7, 2011, which are hereby incorporated by reference herein in their entirety.

The invention claimed is:

1. A radiation generating apparatus comprising:
    an envelope having a first window through which radiation is transmitted;
    a radiation tube being held within the envelope, and having a target layer, a target supporting window supporting the target layer, and a radiation shielding member having a protruding portion protruding from the target supporting window toward the first window;
    a thermally conductive member having a higher thermal conductivity than that of the radiation shielding member and connected to the protruding portion of the radiation shielding member; and
    an insulating fluid filling a space between the envelope and the radiation tube,
    wherein the target supporting window is arranged in opposition to the first window, and wherein the radiation is transmitted through the target supporting window, and
    wherein the target supporting window is secured to the thermally conductive member, and wherein the thermally conductive member is connected to the protruding portion of the radiation shielding member at a front side and a rear side with respect to the second window in a tube axis direction.

2. The radiation generating apparatus according to claim 1, wherein the protruding portion defines a radiation transmitting hole arranged in communication with the target supporting window.

3. The radiation generating apparatus according to claim 1, wherein the thermally conductive member is arranged at an outer periphery of the protruding portion of the radiation shielding member.

4. The radiation generating apparatus according to claim 1, wherein the thermally conductive member is arranged at an inner periphery of the protruding portion of the radiation shielding member.

5. The radiation generating apparatus according to claim 1, wherein the thermally conductive member has a smaller density than that of the radiation shielding member.

6. The radiation generating apparatus according to claim 1, wherein
    the thermally conductive member and the radiation shielding member have shapes of co-axial cylinders, and
    the thermally conductive member has a larger thickness in a radial direction than that of the radiation shielding member.

7. The radiation generating apparatus according to claim 1, wherein the insulating fluid is an electrically insulating oil.

8. The radiation generating apparatus according to claim 1, wherein the thermally conductive member is connected to the target supporting window via a brazing material.

9. The radiation generating apparatus according to claim 1, wherein the radiation tube comprises
    an evacuated container, and an electron emitting source arranged within the evacuated container, wherein the target layer is configured to emit radiation in response to an irradiation with an electron emitted from the electron emitting source.

10. The radiation generating apparatus according to claim 1, wherein the radiation shielding member and the thermally conductive member are formed from metals or alloys different from each other.

11. The radiation generating apparatus according to claim 1, wherein the thermally conductive member is formed from a ceramic.

12. The radiation generating apparatus according to claim 1, wherein the thermally conductive member has a fin structure.

13. The radiation generating apparatus according to claim 1, wherein the thermally conductive member is screwed onto the radiation shielding member.

14. The radiation generating apparatus according to claim 1, wherein the thermally conductive member is formed from a carbon series material.

15. The radiation generating apparatus according to claim 9, wherein the target layer and the radiation shielding member are formed from tungsten, and the thermally conductive member is formed from copper.

16. A radiation imaging apparatus comprising:
   the radiation generating apparatus according to claim 1;
   a radiation detector for detecting the radiation emitted from the radiation generating apparatus and transmitted through an object; and
   a control unit for controlling the radiation generating apparatus and the radiation detector.

17. The radiation generating apparatus according to claim 8, wherein the brazing material contains silver.

* * * * *